US005310882A

United States Patent [19]

Chaleff

[11] Patent Number: 5,310,882

[45] Date of Patent: May 10, 1994

[54] SOMATOTROPINS WITH ALTERATIONS IN THE α-HELIX 3 REGION

[75] Inventor: Deborah T. Chaleff, Pennington, N.J.

[73] Assignee: American Cyanamid Company, Wayne, N.J.

[21] Appl. No.: 621,197

[22] Filed: Nov. 30, 1990

[51] Int. Cl.[5] .......................... C12N 15/18; G02B 5/30

[52] U.S. Cl. .................................... 530/399; 530/324; 930/10; 930/120

[58] Field of Search .................. 530/345, 399; 930/10, 930/120

[56] References Cited

FOREIGN PATENT DOCUMENTS 0355460 2/1990 European Pat. Off. .

OTHER PUBLICATIONS

Mutations in the Third α-Helix of Bovine Growth Hormone Dramatically Affect Its Intracellular Distributiion in Vitro and Growth Enhancement in Transgenic Mice. vol. 266: No. 4 (1991) 2252-2258 Wen Y. Chen et al.

Stabilization of an Associated Folding Intermediate of Bovine Growth Hromone by Site-Directed Mutagenesis. Proc. Natl. Acad. vol. 85:3367-3371 (1988) David N. Brems et al.

Solubility of Different Folding Conformers of Bovine Growth Hormone. David N. Brems, Biochemistry (1988) vol. 27: 4541-4546.

Landschulz et al., "The DNA binding domain of the rat liver nuclear protein C/EBP is bipartite," Science 243:1681-1688 (1989).

Lewin, Genes IV, Cell Press, Cambridge (1990), pp. 3-18.

Lim et al., "Alternative packing arrangements in the hydrophobic core of the lambda repressor," Nature 339:31-36 (1989).

Folding of Bovine Growth Hormone is Consistent With the Molten Globule Hypothesis. Proteins: Structure, Function, and Genetics 5:93-95 (1989). D. N. Brems and H. A. Havel.

Fluorscence in the Characterization of Bovine Growth Hormone. vol. 78: 98-102 (1966). H. G. Burger, H. Edelhoch and P. G. Condliffe.

Characterization of an Associated Equilibrium Folding Intermediate of Bovine Growth Hormone. Biochemistry (1986) vol. 25:6539-6543. D. N. Brems et al.

Three-Dimensional Structure of a Genetically Engineered Variant of Porcine Growth Hormone. P.N.A.S. vol. 84:6434-6437, (1987). Sherin S. Abdel-Meguid et al.

Nucleotide Sequence of the Yeast Regulatory Gene STE7 Predicts a Protein Homologous to Protein Kinases. P.N.A.S. vol. 83: 7371-7375 (1986), M. A. Teague et al.

Expression of a Mutated Bovine Growth Hormone Gene Suppresses Growth of Transgenic Mice. Cell Bio. vol. 87:5061-5065 (1990) W. Y. Chen, D. C. Wight, T. E. Wagner and J. J. Kopchick.

Sequences that Regulate the Divergent GAL1-GAL10 Promoter in Saccharomyces Cerevisiae. Mol. Cell Bio. vol. 4, No. 8: 1440-1448 (1984). Mark Johnston and Roland W. Davis.

Glycine 119 of Bovine Growth Hormone is Critical of Growth-Promoting Activity. vol. 5, No. 12:1845-1852 Mol Endo. (1991). Wen Y. Chen et al.

(List continued on next page.)

*Primary Examiner*—F. T. Moezie
*Attorney, Agent, or Firm*—Estelle J. Tsevdos

[57] ABSTRACT

The present invention relates to somatotropin analogues with amino acid changes in the α-helix 3 regions of said somatotropins, changes in the α-helix 2 regions, combinations thereof plus combinations with other changes to the native amino acid sequence of somatotropins. The resulting analogues are stable for formulation in sustained release, formulations, while maintaining biological activity. Further, methods for conducting site-directed mutagenesis on DNA encoding proteins and/or polypeptides also are provided.

10 Claims, 5 Drawing Sheets

OTHER PUBLICATIONS

Functional Antagonism between Endogenous Mouse Growth Hormone (GH) and a GH Analog Results in Dwarf Transgenic Mice. Endo. vol. 129, No. 3:1402–1408 (1991). Wen Y. Chen et al.

The Megaprimer Method of Site-Directed Mutagenesis. Bio-Techniques vol. 8 No. 4: (1990) 404–407, Gobinda Sarkar, Steve S. Sommer.

Methods of Yeast Genetics (Laboratory Course Manual) (1986) Fred Sherman, Gerald R. Fink, and James B. Hicks. 163–167.

Seeburg et al., *DNA*, 2(1), 37–45, 1983.

Watahiki et al., *The Journal of Biological Chemistry*, 264(1), 312–316, 1989.

Necessary et al., *Biol. Abst.* No. 80:002951. Mol. Cell Endocrinology, 39(3), 247–254, 1985.

YEAST EXPRESSION PLASMID YEp352-pST-I122L

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 579 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 1..579

( x i ) SEQUENCE DESCRIPTION: SEQ ID NO:1:

```
ATG GAT CAA TTC CCA GCC ATG CCC TTG TCC AGC CTA TTT GCC AAC GCC     48
Met Asp Gln Phe Pro Ala Met Pro Leu Ser Ser Leu Phe Ala Asn Ala
  1               5                  10                  15

GTG CTC CGG GCC CAG CAC CTG CAC CAA CTG GCT GCC GAC ACC TAC AAG     96
Val Leu Arg Ala Gln His Leu His Gln Leu Ala Ala Asp Thr Tyr Lys
             20                  25                  30

GAG TTT GAG CGC GCC TAC ATC CCG GAG GGA CAG AGG TAC TCC ATC CAG    144
Glu Phe Glu Arg Ala Tyr Ile Pro Glu Gly Gln Arg Tyr Ser Ile Gln
         35                  40                  45

AAC GCC CAG GCT GCC TTC TGC TTC TCG GAG ACC ATC CCG GCC CCC ACG    192
Asn Ala Gln Ala Ala Phe Cys Phe Ser Glu Thr Ile Pro Ala Pro Thr
     50                  55                  60
```

-continued

```
GGC AAG GAC GAG GCC CAG CAG AGA TCG GAC GTG GAG CTG CTG CGC TTC    240
Gly Lys Asp Glu Ala Gln Gln Arg Ser Asp Val Glu Leu Leu Arg Phe
 65                  70                  75                  80

TCG CTG CTG CTC ATC CAG TCG TGG CTC GGG CCC GTG CAG TTC CTC AGC    288
Ser Leu Leu Leu Ile Gln Ser Trp Leu Gly Pro Val Gln Phe Leu Ser
                 85                  90                  95

AGG GTC TTC ACC AAC AGC CTG GTG TTT GGC ACC TCA GAC CGC GTC TAC    336
Arg Val Phe Thr Asn Ser Leu Val Phe Gly Thr Ser Asp Arg Val Tyr
            100                 105                 110

GAG AAG CTG AAG GAC CTG GAG GAG GGC ATC CAG GCC CTG ATG CGG GAG    384
Glu Lys Leu Lys Asp Leu Glu Glu Gly Ile Gln Ala Leu Met Arg Glu
        115                 120                 125

CTG GAG GAT GGC AGC CCC CGG GCA GGA CAG ATC CTC AAG CAA ACC TAC    432
Leu Glu Asp Gly Ser Pro Arg Ala Gly Gln Ile Leu Lys Gln Thr Tyr
    130                 135                 140

GAC AAA TTT GAC ACA AAC TTG CGC AGT GAT GAC GCG CTG CTT AAG AAC    480
Asp Lys Phe Asp Thr Asn Leu Arg Ser Asp Asp Ala Leu Leu Lys Asn
145                 150                 155                 160

TAC GGG CTG CTC TCC TGC TTC AAG AAG GAC CTG CAC AAG GCT GAG ACA    528
Tyr Gly Leu Leu Ser Cys Phe Lys Lys Asp Leu His Lys Ala Glu Thr
                165                 170                 175

TAC CTG CGG GTC ATG AAG TGT CGC CGC TTC GTG GAG AGC AGC TGT GCC    576
Tyr Leu Arg Val Met Lys Cys Arg Arg Phe Val Glu Ser Ser Cys Ala
            180                 185                 190

TTC                                                                579
Phe
```

( 2 ) INFORMATION FOR SEQ ID NO:2:

( i ) SEQUENCE CHARACTERISTICS:

( A ) LENGTH: 193 amino acids ( B ) TYPE: amino acid ( D ) TOPOLOGY: linear ( i i ) MOLECULE TYPE: protein ( x i ) SEQUENCE DESCRIPTION: SEQ ID NO:2:

```
Met Asp Gln Phe Pro Ala Met Pro Leu Ser Ser Leu Phe Ala Asn Ala
  1               5                  10                  15

Val Leu Arg Ala Gln His Leu His Gln Leu Ala Ala Asp Thr Tyr Lys
             20                  25                  30

Glu Phe Glu Arg Ala Tyr Ile Pro Glu Gly Gln Arg Tyr Ser Ile Gln
         35                  40                  45

Asn Ala Gln Ala Ala Phe Cys Phe Ser Glu Thr Ile Pro Ala Pro Thr
     50                  55                  60

Gly Lys Asp Glu Ala Gln Gln Arg Ser Asp Val Glu Leu Leu Arg Phe
 65                  70                  75                  80

Ser Leu Leu Leu Ile Gln Ser Trp Leu Gly Pro Val Gln Phe Leu Ser
                 85                  90                  95

Arg Val Phe Thr Asn Ser Leu Val Phe Gly Thr Ser Asp Arg Val Tyr
            100                 105                 110

Glu Lys Leu Lys Asp Leu Glu Glu Gly Ile Gln Ala Leu Met Arg Glu
        115                 120                 125

Leu Glu Asp Gly Ser Pro Arg Ala Gly Gln Ile Leu Lys Gln Thr Tyr
    130                 135                 140

Asp Lys Phe Asp Thr Asn Leu Arg Ser Asp Asp Ala Leu Leu Lys Asn
145                 150                 155                 160

Tyr Gly Leu Leu Ser Cys Phe Lys Lys Asp Leu His Lys Ala Glu Thr
                165                 170                 175

Tyr Leu Arg Val Met Lys Cys Arg Arg Phe Val Glu Ser Ser Cys Ala
```

-continued

| 180 | 185 | 190 |
|---|---|---|

Phe

SOMATOTROPINS WITH ALTERATIONS IN THE α-HELIX 3 REGION

BACKGROUND OF THE INVENTION

The present invention relates to somatotropin analogues with amino acid changes in the alpha-helix 3 and/or alpha-helix 2 portion of said somatotropins and to methods for producing the changes in the alpha-helix 3, as well as other regions, of recombinantly-produced polypeptides or proteins. Administration of exogenous somatotropins significantly increases the growth performance of a variety of animals, in particular livestock animals such as swine, but also fish species, as well. This growth enhancement in livestock in particular is usually characterized by an increase in muscle mass accretion concomitant with a decrease in fat, resulting in larger, leaner animals. The feed efficiency of animals receiving exogenous somatotropin also is significantly improved, resulting from an increase in weight gain and a concomitant decrease in feed consumption.

Exogenous administration of somatotropin is achieved in several ways, such as daily injections. In certain instances, however, other routes of administration may be preferred. For instance, an implanted device which allows sustained release of somatotropin over a defined time period may be helpful when treating certain livestock. A more desired route of administration is via an implanted device that allows sustained release over a defined period of time. Such a device would contain large amounts of somatotropin in very high concentrations (ca 500 mg/ml). Further, a somatotropin molecule having high solubility and a low tendency to form insoluble, biologically inactive aggregates is required for such delivery uses.

Somatotropins contain four α-helices which assemble to form an α-helical bundle (Abdel-Meguid et al, 1987). Typically, amino acid side chains projecting into the core of this structure are non-polar, hydrophobic and very tightly packed together in order to exclude penetration of a polar solvent (such as water or saline) into the center of the bundle. In the case of bovine somatotropin, which is related to porcine somatotropin in primary sequence, exposure of the hydrophobic face of α-helix 3 (from amino acid residues $tyr_{110}$ to $leu_{127}$) under protein concentrations in excess of 1 mg/ml promotes the formation of "associative intermediates", which are hypothesized to be a nucleating event in aggregate formation (Brems et al 1986; Brems, 1988). These associative intermediates may represent alternate packing arrangements of this α-helix from several individual somatotropin molecules, resulting in a multimeric structure in which the hydrophobic faces of this helix are resequestered from the aqueous environment. Formation of the associative intermediates can be blocked by addition of an excess of a protein fragment-containing α-helix 3 (Brems, et al, 1986). In addition, extending the hydrophobic face of this helix, by replacing lysine at position 112 with leucine, greatly exacerbates the tendency to form associative intermediates (Brems, 1988).

The present invention addresses the problem of low solubility of somatotropins by altering the α-helix 3 regions of the somatotropins. Specifically, porcine somatotropins with enhanced solution stability in vitro are made by site-directed mutagenesis of α-helix 3. Both the hydrophobic and hydrophilic faces are targeted for mutagenesis. Recently site-directed mutations in the α-helix 3 region of bovine somatotropin resulted in suppressed growth of transgenic mice expressing the mutant somatotropin, a result suggesting that the α-helix 3 region is a region important for biological activity (Chen et al., 1990).

In addition, α-helix 3 mutations are combined, where appropriate, with mutations in the helix 1 or helix 2 regions, and with double mutations in the DNA encoding cysteine at positions 183 and 191, where DNA encoding cysteine is replaced with either alanine or glutamic acid encoding DNA. The double mutations at positions 183 and 191 are described in EP355460. Through the use of the mutations disclosed herein, somatotropins with enhanced solubility (stability), and thereby enhanced properties for sustained release, are provided. Porcine somatotropin is particularly useful in a sustained release form, and as such is a somatotropin of primary interest.

A particularly useful example of the present mutation is mutation I122L, in which the isoleucine at position 122 in α-helix 3 is replaced with leucine. In combination with other mutations at positions 183 and 191 where the cysteines are replaced by alanine, a significant increase in the transition temperature of the protein's single tryptophan residue is obtained. The transition temperature is a measure of the thermal stability of the protein. In one of the most preferred mutation, enhanced solution stability is obtained when the I122L mutation is combined with mutations in which the cysteine-encoding DNA at positions 183 and 191 are altered to encode glutamic acid.

SUMMARY OF THE INVENTION

Figure 1:
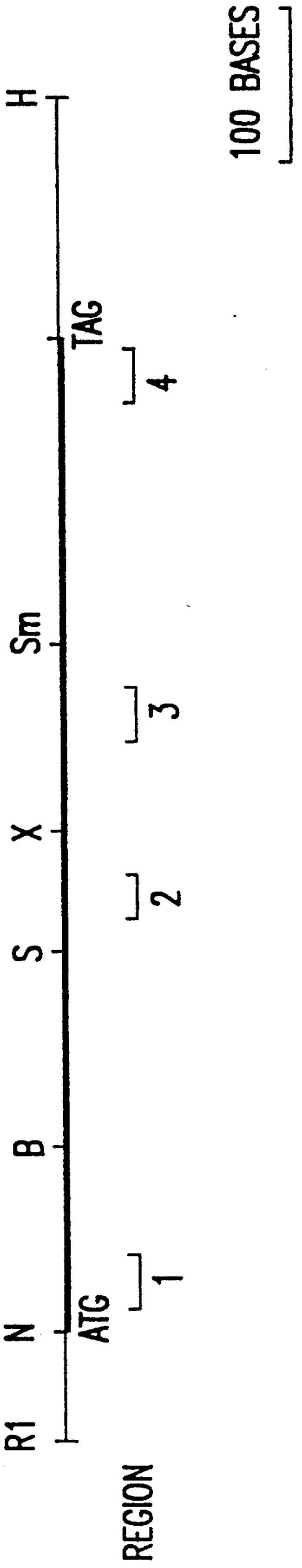
FIG. 1: Restriction map of recombinant porcine somatotropin (rpST) DNA. The wide solid line represents the amino acid-encoding portion of rpST DNA; the slender line represents the 5' and 3' flanking, non-coding DNA sequence. Regions of rpST gene subject to site directed mutagenesis are numbered and indicated below the restriciton map, in which number 1 represents DNA encoding α-helix 1, number 2 represents DNA encoding α-helix 2, number 3 represents DNA encoding α-helix 3 and number 4 represents the DNA encoding the cysteines present at positions 183 and 191. The letters above the map denote the location of various restriction endonuclease restriction sites, in which RI=EcoRI, N=NdeI, B=BssHII, S=SacI, X=XbaI, Sm=SmaI and H=HindIII.
Figure 2:
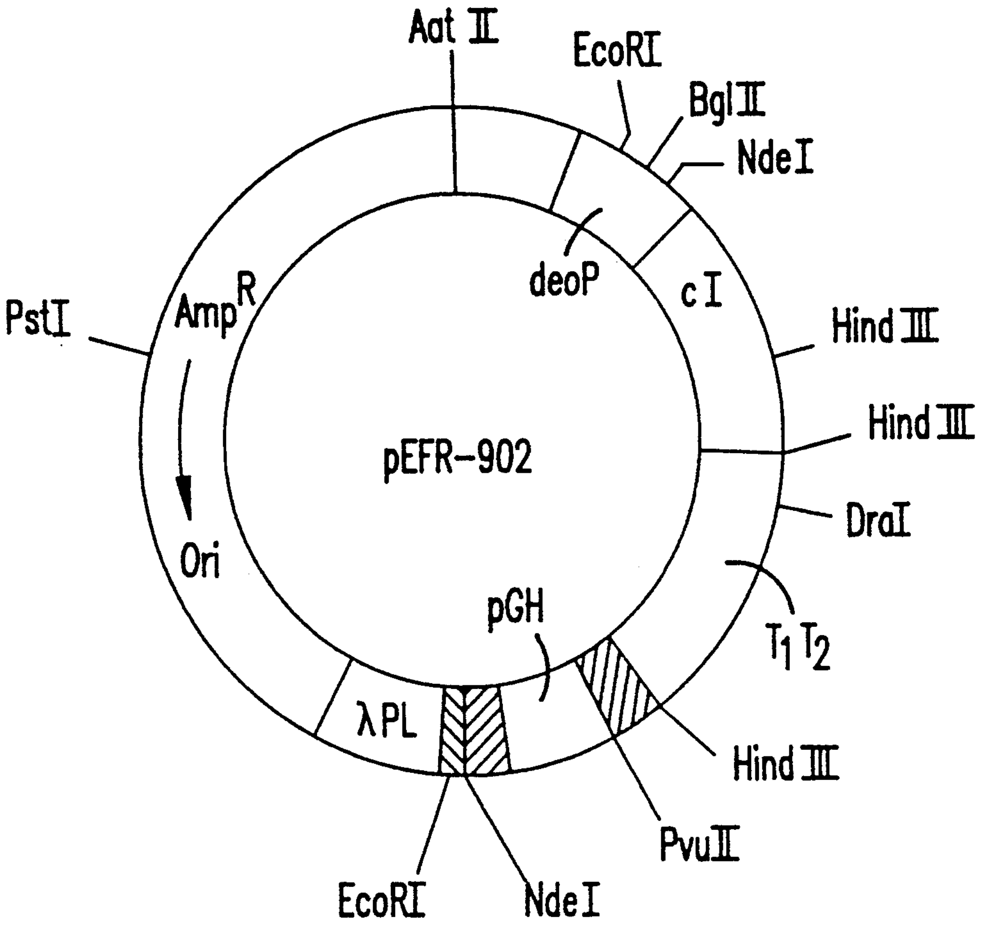
FIG. 2: Structure and restriction map of plasmid pEFF-902. This plasmid contains the pBR322 replication origin (Ori) and ampicillin resistance gene, the $\lambda P_L$ promoter, the cII ribosome binding site and cI repressor gene from bacteriophage λ, the $T_1T_2$ transcription terminator from the *E. coli* rrnB operon, a 60-base pair sequence from the deo regulatory region without promoters, and the rpST gene denoted as pGH. Relevant restriction sites are indicated. The rpST-containing DNA is excised from this plasmid by treatment with EcoRI and HindIII and cloned into mutagenesis vector pGEM3z(f+) as described in the text.
Figure 3:
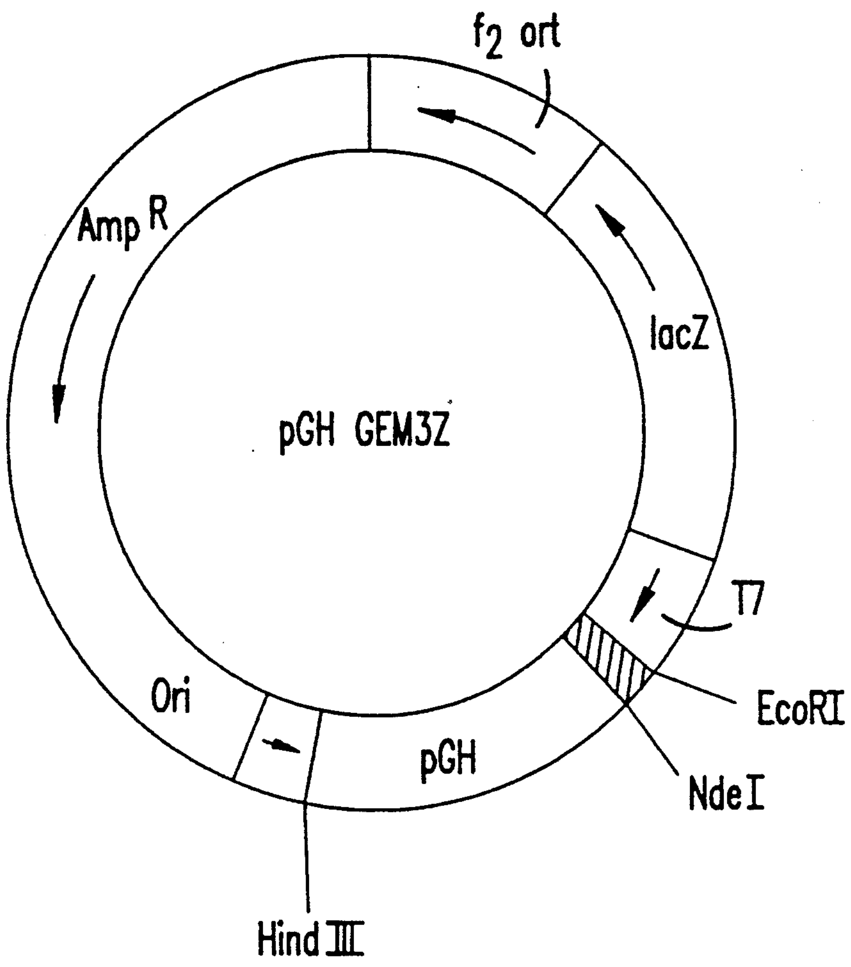
FIG. 3: Structure and partial restriction map of pGHGEM3Z. This phagemid contains the f1 DNA replication origin, the pBR322 replication origin (Ori) and ampicillin resistance gene, the SP6 and T7 promoters, the lacZ gene cII ribosome binding site from bacteriophage λ and the rpST gene, denoted rpGH. Single stranded phagemid DNA is used as the template for site directed mutagenesis as described in the text.

The present invention relates to somatotropin(s) with amino acid sequence changes in the α-helix 3 and/or α-helix 2 regions of the somatotropin molecule. The resulting somatotropin is more stable (soluble) than the native form of the somatotropin and maintains biological activity when formulated as a sustained release formulation of said somatotropin. More specifically, the somatotropins of the present invention include human, bovine, porcine, ovine, caprine, equine, fish and avian somatotropins. Further, the term somatotropin encompasses deletions, additions and alterations to other portions of the native somatotropin molecule. For instance, modified (substituted or eliminated cysteines) or derivatized somatotropins in which one to four of the cysteine amino acid residues of said somatotropin are replaced by from one to four amino acid residues, separately selected from the amino acids, arginine, lysine, aspartic acid, glutamic acid, asparagine, glutamine, histidine, alanine, glycine, isoleucine, leucine, valine, phenylalanine, tryptophan, tyrosine, methionine, serine, threonine or proline; or in which all four cysteines are converted to cysteic acid.

It is an object of the present invention, therefore, to provide novel somatotropins which are more soluble than the native form of the molecule and are thus biologically effective when formulated, preferably in sustained release formulations. It is a further object of the present invention to provide site-directed mutagenesis techniques for making the somatotropins of the present invention, as well as other recombinantly-produced polypeptides and/or proteins. These and further objects of the invention will be apparent by the following detailed description of the invention.

The plasmids, DNA sequences and microorganisms deposited in connection with the present patent application, except where specified to the contrary, are deposited in American Cyanamid Company's culture collection maintained in Princeton, N.J. and are deposited pursuant to the Budapest Treaty with the American Type Culture Collection (ATCC) in Rockville, Md. 20852, U.S.A.

The DNA strains referred to hereinabove were deposited in the ATCC on Aug. 23, 1988. They are pGEMpST-SX (ATCC number 40482), pRO211 (ATCC number 40483) and pEFF-902 (ATCC number 40484). It is recognized by those skilled in the art that these DNAs can be inserted into any appropriate expression system to obtain the somatotropins of the invention or mutations thereof.

The *E. coli* K12 bacterial strains expressing some of the novel animal somatotropins of the present invention also were deposited in the ATCC on Aug. 23, 1988. The bacterial strains include *E. coli* strain 1655 (ATCC number 67762), 1655/pROpSTA34 (ATCC number 67763), 1655/pROpSTE34 (ATCC number 67764), 1655/pROpST (ATCC number 67765), 4200 (ATCC number 67766), 4200/pROpSTA34 (ATCC number 67767), 4200/pROpSTE34 (ATCC number 67768), 420/pROpST (ATCC number 67769), 4255 (ATCC number 67770), 4255/pROpSTA34 (ATCC number 67771, 4255/pROpSTE34 (ATCC number 67772), 4255/pROpST (ATCC number 67773) and 4300 (ATCC number 67774).

The following *E. coli* K12 bacterial strains also were deposited in the ATCC on Sep. 21, 1990. These include pROpST-SXE-Q21HH22R (ATCC 68410), pROpST-SXE-G121A (ATCC 64811), pROpST-SXE-A6TS11R (ATCC 68412), pROpST-SXA-S81, 87L+I122L (ATCC 68413), pROpST-SXA-S81,87L (ATCC 68414), pROpST-SXA-L82,84Q+L115K (ATCC 68415), pROpST-SXA-L82, 84Q (ATCC 68416), pROpST-SXE-I122L (ATCC 68417), pROpST-SXA-I122L (ATCC 68418), pST-SX (ATCC 68419), pROpST-SXA-L118E (ATCC 68420), pROpST-SXA-E119LQ123L (ATCC 68421), pROpST-SXA-I122E (ATCC 68422), pROpST-SXA-M126A (ATCC 68423) and pROpST-SXE-A6TS11R+I122L (ATCC 68424).

DETAILED DESCRIPTION OF THE INVENTION

The animal somatotropins of the present invention are provided by site directed mutagenesis, but other means such as chemically synthesizing the peptides and/or proteins may be employed in producing said somatotropins. Currently-utilized techniques for the alteration of the DNA sequence of a cloned segment of DNA at a specific defined site require the production of a single stranded form of that DNA. The single stranded DNA is annealed to a synthetic oligonucleotide which is complementary to a portion of that DNA except that the oligonucleotide contains within it a region of mismatch. The region of mismatch is usually located in the central portion of the oligonucleotide. In some instances, the oligonucleotide also contains a restriction endonuclease recognition site at or near the site of the mutation(s). The annealed mixture is then made double stranded and covalently closed by the addition of *E. coli* DNA polymerase I, large fragment and deoxynucleotide triphosphates in the presence of T4 DNA ligase and adenosine 5' triphosphate. The double stranded DNA is then transformed into an appropriate *E. coli* strain where the mismatched region of the DNA is repaired and replicated.

Two populations of clones are obtained. Depending on which strand is chosen as the template for repair synthesis, a clone either contains the wild type or the altered (mutated) sequence. The clones which contain the mutated sequence, that which corresponds to the sequence of the oligonucleotide, are selected by hybridization to the radioactively-labelled oligonucleotide. Due to mismatch between the oligonucleotide and the wild type sequence, the radioactively-labelled oligonucleotide is more stably bound to the clones which contain the mutated sequence. Incubation at an appropriate temperature therefore discriminates between wild type and mutated clones. In cases in which the oligonucleotide also contains a restriction endonuclease cleavage site, digestion of candidate clones with the cognate restriction endonuclease reveals clones which contain the mutated sequence and provides another means of discriminating between wild type and mutated clones. The alterations in the identified clones then are confirmed by DNA sequencing of the relevant regions.

Restriction fragments of plasmid clones containing the desired mutation(s) are reconstructed into expression plasmids suitable for expressing the mutant gene product in either bacteria or yeast, but not both. This reconstruction is achieved by standard subcloning procedures.

In the following discussions, recombinant porcine somatotropin is selected as representative of the modified recombinant somatotropins of the present invention and the methods employed for their preparation. Further, the following description and examples are illustrative of the present invention and not limited thereof.

The DNA and amino acid sequence of recombinant porcine somatotropin are provided hereinbelow and correspond to Sequence I.D. Nos. 1 and 2, respectively. The most preferred recombinant porcine somatrotropin is a polypeptide sequence of 193 amino acids, in which the $NH_2$-terminus has been modified to include 3 additional amino acids (met, asp, gln) and a deletion of the first amino acid (ala) found in some mature forms of pituitary-derived porcine somatotropin. However the 191 amino acids PST as well as other derivatives thereof, such as deletions at the $NH_2$-terminus, additions thereof, and/or deletions and/or additions at the COOH-terminus are meant to form part of the present invention.

Recombinant pST:

$NH_2$—met—asp—gln—phe—pro—ala-185 amino acids—ala—phe—COOH

Pituitary pST:

$NH_2$—ala—phe—pro—ala-185 amino acids—ala—phe—COOH

This modification results in a net increase of two additional amino acids in the recombinant pST protein and is described in EP355460. The numbering system employed in the description of the mutagenized derivatives of recombinant porcine somatotropin reflects this additional increase, and is easily applied by any practitioner skilled in the art.

Construction of pGEMpST-SX DNA

Single stranded pGEMpST-SX DNA is the template DNA for all of the mutagenesis reactions and is prepared from pGHGEM3Z DNA by site directed mutagenesis. Cloning of the porcine somatotropin (rpST) gene into the phagemid pGEM-3z(f+), resulting in pGHGEM3Z, is achieved by the following general procedure. A fragment of DNA containing the pGHGEM3Z porcine somatotropin (rpST) gene is isolated from the bacterial expression plasmid pEFF-902 by cleavage with the restriction enzymes EcoRI and HindIII (FIG. 1). The rpST gene-containing fragment is then purified by agarose gel electrophoresis. Double stranded phagemid DNA pGEM-3z(f+) is digested with EcoRI and HindIII, treated with calf intestinal EcoRI alkaline phosphatase and the large fragment purified by agarose gel electrophoresis. The two purified fragments are then mixed together and ligated with T4 DNA ligase. The mixture is transformed into bacteria and several resultant colonies grown. Plasmid DNA is prepared by a standard alkaline lysis method and the structure determined by digestion with appropriate restriction enzymes. A clone is isolated which contains the expected fragments and is designated pGHGEM3Z.

pGEMpST-SX

The aim of this mutagenesis is to create an rpST DNA sequence in which the DNA sequence encoding α-helix 2 is bounded on the 5′ side (from positions 225–230 of the DNA coding region) by a SacI restriction site and the 3′ side (from positions 285–290) by an XbaI restriction site. These alterations in the DNA sequence do not change the amino acid sequence of the rpST protein. The presence of these restriction endonuclease cleavage sites results in the creation of a "helix 2 cassette", so that mutations in the helix 2-encoding DNA can be conveniently and rapidly combined with appropriate mutations in the DNA encoding helix 3. The construction pf pGEMpST-SX is described below.

The DNA sequences of synthetic oligonucleotides SacI293 and XbaI353 are described in Table 1. Single stranded pGHGEM3Z DNA is the substrate for mutagenesis and is prepared from purified phage by standard protocols. 2000 ng of this DNA is mixed with 100 ng each of the SacI293 and XbaI353 oligonucleotides, both of which have been phosphorylated at their 5′ ends with adenosine 5′ triphosphate and T4 polynucleotide kinase. The mixture is contained in a total volume of 10 μL in 1X annealing buffer (1X annealing buffer is 75 mM KCl and 5 mM Tris-Cl, pH 8.0). The mixture is heated at 65° C. for 7 minutes followed by a 10 minute incubation at room temperature (RT). This procedure permits the oligonucleotides to anneal to the single stranded substrate (template) DNA. Annealed molecules are extended and converted to covalently closed, double stranded DNA by the addition of 22 μl $H_2O$, 1 μl 20 mM ATP, 2 units each of T4 DNA ligase, and DNA polymerase I large fragment (for unit definition, see New England Biolabs catalogue, 1989), 2 μl 20X dNTP's (a mixture of the four deoxyribonucleotide 5′ triphosphates each at a concentration of 2 mM) and 4 μl 10X "fill in" buffer (1X fill in buffer is 27.5 mM Tris-Cl, pH 7.5, 15 mM $MgCl_2$, 2 mM DTT). After a one hour incubation at room temperature (RT), half of the reaction is introduced into HB101 competent cells by a standard protocol. Single colonies are apparent after overnight incubation at 37° C. Plasmid DNA is prepared by a standard procedure from 24 colonies, and digested, in separate reactions, with SacI and XbaI. Plasmid DNA's containing both restriction sites, which indicated the incorporation of both the SacI293 and XbaI353 oligonucleotides into the rpST gene, are further purified by introduction into HB101 competent cells as described previously. Plasmid DNA is prepared and digested in separate reactions with SacI and XbaI to verify the presence of each restriction site in the plasmid DNA, which is then confirmed by DNA sequence analysis of the relevant regions of the rpST DNA.

TABLE I

| MUTAGENIC OLIGONUCLEOTIDES | | |
|---|---|---|
| Name | Sequence (5'-3') | Mutation |
| SacI293 | GACGTGGAGCTCCTGCGCTTCTCG | Helix 2 cassette |
| XbaI353 | CAGTTCCTCTCTAGAGTCTTCACC | Helix 2 cassette |
| S81L | TGCGCTTCTTGCTGCTGC | S81,87L |
| S87L | TCATCCAGTTGTGGCTCG | S81,87L |
| Q8082 | TGCGCTTCTCGCAGCTGCAGAT CCAGTCGTGG | L82,84Q |
| Q8082D | TTCTCGCAGCTGCAGATCCAGT | L82,84Q detection probe |
| K113 | CTACGAGAAGAAGAAGGACCTG | L115K |
| E116 | GCTGAAGGACGAGGAGGAGGGC | L118E |
| K113E116 | GTCTACGAGAAGAAGAAGGACG AGGAGGAGGGCAT | L115KL118E |
| K113E116D | AGAAGAAGAAGGACGAGGAGGA | K113E116 Probe |
| E116K120 | AAGCTGAAGGACGAGGAGGAGG GCAAGCAGGCCCTGATG | L118EI122K |
| E120 | GGAGGAGGGCGAGCAGGCCCTG | I122E |
| L120-3 | GGAGGAGGGCCTGCAGGCCCTG | I122L |
| A124-2 | CAGGCCCTGGCACGGGAGCTGG | M126A |
| E113EHDQ116 | CGCGTCTACGAGAAGGAGAAGGAC(GC) A(GC)GAGGAGGGCATCCAG | L115E |
| E113D | CGTCTACGAGAAGGAGAAGGAC | L115E construction probe |
| L115A | CTACGAGAAGGCGAAGGACCTG | |
| L118A | GCTGAAGGACGCGGAGGAGGGC | |
| L118TK | CTGAAGGACA(CA)AGAGGAGGGCAT | L118K |
| L118T | CTGAAGGACACTGAGGAGGGC | L118T |
| L117,121 | GAAGGACCTGCTGGAGGGCAT CCTGGCCCTGATG | E119LQ123L |
| Leu117121D | CCTGCTGGAGGGCATCCTGGCC | E119LQ123L probe |
| K114R/AccI | GACCGCGTATACGAGCGTCTGAAGGA | K114R |
| G121A/XmnI | CTGGAGGAAGCTATTCAGGCCCTG | G121A |
| K116R/BglII | AGAAGCTGCGAGATCTGGAGGA | K116R |
| A14D/HindIII | CCTTGTCAAGCTTATTTGACAACGCCG | A14D |
| A6T | TCAATTCCCAACCATGC | A6T |
| S11RA14D/SaI | ATGCCCTTGAGTCGACTAT TTGACAACGCC | S11RA14D |
| Q21HH22R/ClaI | CCGGGCCCATCGATTGCACCAA | Q21HH22R |
| PvuII634 | AGAAGGCAGAGCTGCTGTCCAC | I122L PCR |

Synthesis of Mutations in Helices 1, 2, or 3

Mutagenesis of the rpST gene in pGEMpST-SX is achieved as described below. The aim of the mutagenesis program is to generate an rpST molecule that has a decreased tendency to aggregate at high protein concentrations (>100 mg/ml). The focus is the hydrophobic face of helix 3, from amino acid residues 112 through 129, which is believed to be critical in the initiation of an aggregation reaction (Brems et al, 1986). Because the rpST gene employed here encodes an additional 2 amino acids at the amino-terminus, the total number of amino acid residues is 193, as opposed to the 191 residues found in pituitary-derived bovine and porcine somatotropin. Residues 112 through 129 correspond to residues 110 through 127 of bovine somatotropin (Abdel-Meguid et. al., 1987). Other regions of the molecule that are targeted for mutagenesis are helix 2, from residues 81 through 87, the hydrophilic face of helix 3 and helix 1, from residues 6 through 11. Combination mutants are generated by additional rounds of mutagenesis, or by subcloning relevant regions. The basic protocol used to obtain the L118E mutation and examples of all others are hereinafter described. Variations in the basic protocol are described in the appropriate examples.

Preparation of single stranded substrate pGEMpST-SX DNA is precisely as described for pGHGEM3Z. The DNA sequence of the synthetic mutagenic oligonucleotide used in the construction of mutation L118E, E116, is displayed in Table I and is phosphorylated at its 5' end as described for SacI293. The annealing and fill in reactions are also exactly as described for SacI293 mutagenesis of pGHGEM3Z. After introduction of half of the reaction mix into HB101 competent cells and overnight incubation at 37° C., the resultant colonies are transferred to nitrocellulose filters and processed for hybridization by standard methods. The E116 oligonucleotide is also used for detection of the mutation. It is radioactively labelled at the 5' end with $\gamma$-$^{32}$P-ATP and polynucleotide kinase. Hybridization is overnight at 37° C. in 5XSSC (1XSSC is 0.15 M sodium chloride, 0.015 M sodium citrate pH7.0), 1X Denhardt's (0.02% each (w/v) Ficoll, bovine serum albumin, polyvinylpyrollidone), 150 $\mu$g/ml yeast tRNA and the radio-labelled probe.

After hybridization, the filters are washed for at least 30 minutes at 37° C. in 5XSSC, followed by two thirty minute washes in TAC (TAC is 3M tetramethyl ammonium chloride, 50 mM (tris) [hydromethyl] aminomethane pH 8.0, 1 mM EDTA (ethylenediamine tetraacetic acid), 0/1% (w/v) sodium dodecyl sulfate) at the desired temperature. The incubation temperature of this latter wash determines the specificity, as the E116 oligonucleotide will remain hybridized only to completely complementary clones. For the E116 oligonucleotide, the temperature is 59.0° C. After exposure to X-Ray film, only those clones which are completely complementary to E116 are observed. Plasmid DNA is prepared from several of these positive scoring colonies, reintroduced into HB101 and screened as described hereinabove. Plasmid DNA from several positives from this second round of screening is prepared and analyzed by DNA sequence analysis; those containing the L118E mutation are thus unambiguously identified. The plasmid bearing this mutation is designated pGEMpST-SX-L118E.

Figure 4:
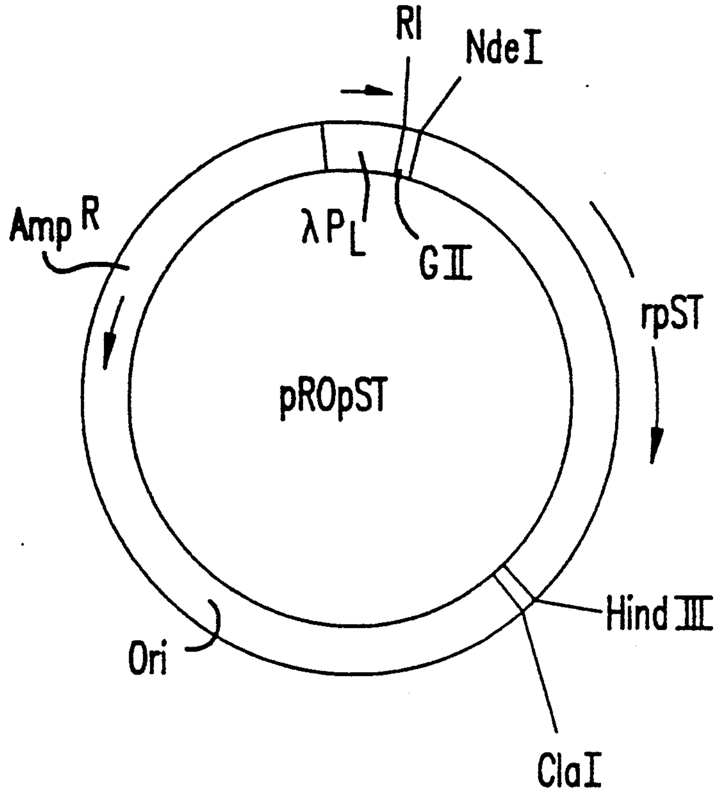
FIG. 4: Bacterial expression plasmid pROpST is used for production of recombinant porcine somatotropins in bacteria (*E. coli*). The cII ribosome binding site is located between the EcoRI and NdeI restriction sites. The translational initiation codon for rpST is embedded in the NdeI site. Expression is driven by the $\lambda P_L$ promoter.

The resultant rpST gene clones containing the L118E mutation are transferred into each of two expression vectors, pROpST-SX and pROpST-SXA, whose constructions are described. The object of these constructions is to introduce the rpST gene containing the helix 2 cassette, defined by the presence of the SacI and XbaI restriction sites previously described, into a plasmid vector designed for expression of the rpST gene in *E. coli.* An additional objective is to introduce the mutations described in the present invention into each of two different rpST genetic backgrounds. One is natural (wild type) with respect to the presence of each of two cysteine residues at positions 183 and 191. The other rpST gene encodes alanine instead of cysteine at these same positions and is described in EPO 355460. Plasmid pROpSTA34 (FIG. 4) contains an EcoRI/HindIII fragment cloned into expression plasmid pRO211. This EcoRI/HindIII fragment carries an altered rpST gene, in which the DNA encoding the cysteines at positions 183 and 191 has been mutated to alanine-encoding DNA in these positions. It thus carries the ala, ala mutations. Plasmid pROpSTA34 is digested with EcoRI and HindIII in one reaction mixture and EcoRI and SmaI in another. The large, vector- containing fragment is purified from each reaction by agarose gel electrophoresis. Plasmid pROpST-SX, which contains the helix 2 cassette in the otherwise wild type rpST background, is generated by ligation of the purified EcoRI/HindIII fragment from pGEMpST-SX. The ligation mixture is introduced into bacterial strain N99cI. In this strain, rpST expression is driven by the λPL promoter, is prevented by the presence of the wild type λ repressor. Resultant plasmid clones with the desired construction are identified by digestion with the appropriate restriction enzymes. Plasmid pROpST-SXA, which contains the helix 2 cassette in the mutated rpST gene, is generated from ligation of the purified EcoRI/SmaI vector fragment from pROpSTA34 with the purified EcoRI/SmaI fragment from pGEMpST-SX. The ligation mixture is introduced into bacterial strain N99cI, and the resultant plasmid clones analyzed by digestion with the relevant restriction enzymes to identify the desired plasmid clones.

The L118E mutation is introduced into expression plasmids pROpST-SX and pROpST-SXA by cleaving pGEMpST-SX-L118E DNA with EcoRI and HindIII in one set of reactions, and EcoRI and SmaI in the other set of reactions. The small, rpST-bearing fragments from each reaction mixture contain the L118E mutation and are purified by agarose gel electrophoresis. Plasmid pROpST-SX is restricted with EcoRI and HindIII, and the large vector-bearing fragment is purified by agarose gel electrophoresis. This fragment is ligated with the purified EcoRI/HindIII fragment from pGEMpST-SX-L118E, resulting in plasmid pROpST-SX-L118E. The ligation mix is transformed into expression strain 4300, which carries a temperature-sensitive λ repressor. In these strains, rpST expression depends on temperature. At 42° C. the λ repressor is inactive, permitting expression from the $\lambda P_L$ promoter. Bacterial colonies carrying the pROpST-SX-L118E plasmid are identified by their ability to produce the rpST protein at 42° C. (the non-permissive temperature for the λ repressor). Plasmid pROpST-SXA is restricted with both EcoRI and SmaI, and the large vector fragment is purified by agarose gel electrophoresis. This fragment is ligated with the purified EcoRI/SmaI fragment from pGEMpST-SX-L118E, resulting in plasmid pROpST-SXA-L118E. The ligation mix is transformed into expression strain 4300, and bacterial colonies carrying the pROpST-SXA-L118E plasmid are identified by their ability to produce the rpST protein at 42° C.

EXAMPLE 1 CREATION OF A HELIX 2 "CASSETTE" USING TWO SYNTHETIC OLIGONUCLEOTIDES SIMULTANEOUSLY

The aim of this mutagenesis is to create an rpST DNA sequence in which the DNA sequence encoding α-helix 2 is bounded on the 5' side (from positions 225–230 of the DNA coding region) by a SacI restriction site and the 3' side (from positions 285–290) by an XbaI restriction site. These alterations in the DNA sequence do not change the amino acid sequence of rpST. The presence of these restriction endonuclease cleavage sites results in the creation of a "helix 2 cassette", so that mutations in the helix 2-encoding DNA are conveniently and rapidly combined with appropriate mutations in the DNA encoding helix 3. The construction of pGEMpST-SX is as described hereinabove.

EXAMPLE 2

SUBSTITUTION OF HYDROPHOBIC AMINO ACIDS OF HELIX 3 WITH HYDROPHILIC AMINO ACIDS THAT STABILIZE α HELICES WITH MUTAGENIC OLIGONUCLEOTIDES

The members of this mutational class include mutations L118E, L115K, L115KL118E and L118EI122K. The mutations are generated precisely as described for L118E in the basic protocol. The resultant plasmids bearing these mutations are designated pGEMpST-SX-L118E, pGEMpST-SX-L115K, pGEMpST-SX-L115KL118E and pGEMpST-SX-L118EI122K, respectively.

The generation of the L115K mutation in rpST is achieved precisely as described for L118E, except that mutagenic oligonucleotide K113, displayed in Table I is used both in the mutagenesis and hybridization reactions. This oligonucleotide alters the rpST sequence so that the codon for leucine at position 115 is changed from CTG to AAG which encodes lysine.

The generation of the L115KL118E mutation in rpST is achieved precisely as described for L118E, except that mutagenic oligonucleotide K113E116 displayed in Table I is used in the mutagenesis reaction and oligonucleotide K113E116D, displayed in Table I is used in the hybridization reaction. The K113E116 oligonucleotide alters the rpST sequence so that the codon for leucine at position 115 is changed from CTG to AAG which encodes lysine, and the leucine codon at 118 is changed from CTG to GAG which encodes glutamic acid. This oligonucleotide thus creates a double mutation in the rpST DNA sequence.

The generation of the L118EI122K mutation in rpST is achieved precisely as described for L118E, except that mutagenic oligonucleotide E116I120 displayed in Table I, is used in the hybridization reactions. The E116K120 oligonucleotide alters the rpST sequence so that the codon for leucine at position 118 is changed from CTG to GAG which encodes glutamic acid, and the isoleucine codon at 120 is changed from ATC to AAG, which encodes lysine. This oligonucleotide thus creates a double mutation in the rpST DNA sequence.

EXAMPLE 3

SUBSTITUTION OF HYDROPHOBIC AMINO ACIDS IN HELIX 3 WITH HYDROPHILIC AMINO ACIDS WITH MUTAGENIC OLIGONUCLEOTIDES

The members of this mutational class include I122E, L118T, L118K and L115E. The plasmids bearing these mutations are designated pGEMpST-SX-I122E, pGEMpST-SX-L118T, pGEMpST-SX-L118K and PGEMpST-SX-L115E, respectively. The construction of these mutations is performed precisely as described for L118E except for the oligonucleotides used in both the mutagenesis and hybridization reactions, whose sequences are displayed in Table I.

Mutagenic oligonucleotide E120 is used in the construction of mutation I122E (Table I). This oligonucleotide alters the sequence of the rpST gene such that the codon for isoleucine at position 122 is converted from ATC to GAG which encodes glutamic acid. The E120 oligonucleotide is also used as the radio-labelled detection probe in the hybridization reactions, which in all other respects are identical to those described above for L118E, except that the nitrocellulose filters are incubated in TAC buffer at 56° C. The construction of mutation L118T is performed precisely as described for L118E except that the oligonucleotide used in both the mutagenesis and hybridization reactions is L118T (Table I). This oligonucleotide alters the sequence of the rpST gene such that the codon for leucine at position 118 is converted from CTG to ACT which encodes threonine. Plasmids containing the desired mutation are distinguished from non-mutation bearing plasmids after the nitrocellulose filters are incubated in TAC buffer at 56° C.

The generation of the L115E mutation in rpST is achieved precisely as described for L118E, except that mutagenic oligonucleotide E113EHDQ116, displayed in Table I, is used in the mutagenesis reaction and oligonucleotide E113D, displayed in Table I, is used in the hybridization reactions. The E113EHDQ116 oligonucleotide alters the rpST sequence so that the codon for leucine at position 115 is changed from CTG to GAG which encodes glutamic acid, and the leucine codon at 118 is changed from CTG to GAG, which encodes glutamic acid, GAG, which encodes glutamic acid, GAC, which encodes aspartic acid, CAC, which encodes histidine or CAG, which encodes glutamine. The variety of mutational changes that occur at position 118 is due to the fact that the mutagenic oligonucleotide is a mixture of four oligonucleotides, generated during the synthesis of the oligonucleotide. DNA sequencing of the resultant plasmid clones that hybridize to the E113D radio-labelled hybridization probe reveal that they contain the L115E mutation, but none carry any of the four possible mutations at position 118. Thus, this mutagenesis results in only a single mutation at position 115.

The generation of the L118K mutation in rpST is achieved precisely as described for L118E, except that mutagenic oligonucleotide L118TK, whose sequence is displayed in Table I, is used. The L118TK oligonucleotide alters the rpST sequence so that the codon for leucine at position 118 is changed from CTG to AAG which encodes lysine or from CTG to CAG, which encodes threonine. The various possibilities for the mutational changes that arise at position 118 are due to the fact that the mutagenic oligonucleotide is a mixture of two oligonucleotides, generated during the synthesis of the oligonucleotide. DNA sequencing of the resultant plasmid clones that hybridize to the L118TK radio-labelled hybridization probe reveal that they contain the L115K mutation, and none carry the other possible mutations, L118T, at position 118. Thus, this mutagenesis results in a single mutation at position 118.

EXAMPLE 4

SUBSTITUTION OF HYDROPHILIC AMINO ACIDS IN HELIX 3 WITH HYDROPHOBIC AMINO ACIDS USING A MUTAGENIC OLIGONUCLEOTIDE

The single member of this mutational class is the double mutant, E119LQ123L. The plasmid bearing this mutation, confirmed by DNA sequence analysis, is PGEMpST-SX-E119LQ123L. The construction of this double mutant rpST gene is achieved as described for L118E except that mutagenic oligonucleotide L117,121 is used (Table I). This oligonucleotide alters the rpST DNA sequence such that the DNA encoding glutamic acid is changed from GAG to CTG, which encodes leucine, and the DNA encoding glutamine at position 123 is changed from CAG to CTG which encodes leucine. The mutagenesis reaction utilizes this oligonucleotide, while Leu117121D, whose sequence is displayed in Table I is used as the radio-labelled probe in the hybridization reactions. All of the procedures used in the construction of this mutation are as previously described for L118E, except that the nitrocellulose filters are incubated in TAC at 58° C. to detect mutation-bearing plasmids.

EXAMPLE 5

SUBSTITUTION OF NON-POLAR AMINO ACIDS WITH LARGE SIDE CHAINS IN HELIX 3 WITH NON-POLAR AMINO ACIDS WITH SMALL SIDE CHAINS

The members of this mutational class include L115A, L118A and M126A. The plasmids bearing these mutations are designated pGEMpST-SX-L115A, pGEMpST-SX-L118A and pGEMpST-SX-M126A, respectively. The construction of these mutations is performed precisely as described for L118E except for the mutagenic oligonucleotides employed and, if necessary, the TAC wash temperature.

The DNA sequence of the synthetic mutagenic oligonucleotide used in the construction of mutation L115A, L115A, is displayed in Table I. This oligonucleotide alters the sequence of the rpST gene such that the codon for leucine at position 115 is converted from CTG to GCG which encodes alanine. The L115A oligonucleotide is also used as the radio-labelled detection probe in the hybridization reactions. Plasmids containing the desired mutation are distinguished from non-mutation-bearing plasmids after nitrocellulose filters are incubated in TAC buffer at 56° C.

The generation of the L118A mutation in rpST is achieved precisely as described for L118E, except that the mutagenic oligonucleotide employed in both the mutagenesis and hybridization/screening reactions is L118A, whose sequence is displayed in Table I. The L118A oligonucleotide alters the rpST sequence so that the codon for leucine at position 118 is changed from CTG to GCG which encodes alanine. Mutation-bearing plasmids are detected by incubating the nitrocellulose in TAC buffer at 56° C. The plasmid bearing this mutation, confirmed by DNA sequence analysis, is designated pGEMpST-SX-L118A..

The generation of the M126A mutation in rpST is achieved precisely as described for L118E, except that the mutagenic oligonucleotide employed in both the mutagenesis and hybridization/screening reactions is A124-2, whose sequence is displayed in Table I. The A124-2 oligonucleotide alters the rpST sequence so that the codon for methionine at position 126 is changed from ATG to GCA which encodes alanine. Mutation-bearing plasmids are detected by incubating the nitrocellulose filters in TAC buffer at 56° C. The plasmid bearing this mutation, confirmed by DNA sequence analysis, is designated pGEMpST-SX-M126A.

EXAMPLE 6

SUBSTITUTION OF ISOLEUCINE 122 WITH LEUCINE

The members of this mutational class include I122L, I122LL118A and I122LM126A. The plasmids bearing these mutations are designated pGEMpST-SX-I122L, pGEMpST-SX-I122LL118A and pGEMpST-SX-I122LM126A, respectively. The construction of these mutations is performed precisely as described for L118E except for the mutagenic oligonucleotides employed and, if necessary, the TAC wash temperature.

The DNA sequence of the synthetic mutagenic oligonucleotide used in the construction of mutation I122L, L120-3, is displayed in Table I. This oligonucleotide alters the sequence of the rpST gene such that the codon for isoleucine at position 122 is converted from ATC to CTG which encodes leucine. The L120-3 oligonucleotide is also used as the radio-labelled detection probe in the hybridization reactions. Plasmids containing the desired mutation are distinguished from non-mutation-bearing plasmids after nitrocellulose filters are incubated in TAC buffer at 56° C.

The generation of the I122LL118A mutation in rpST is achieved precisely as described for L118E, except that the mutagenic oligonucleotide employed in both the mutagenesis and hybridization/screening reactions is L118A, and the template DNA used for mutagenesis is pGEMpST-SX-I122L. The template DNA is prepared precisely as described for pGEMpST-SX DNA. Mutation-bearing plasmids are detected by incubating the nitrocellulose filters in TAC buffer at 56° C. The plasmid bearing this mutation, confirmed by DNA sequence analysis, is designated pGEMpST-SX-L118AI122L. The generation of the I122LM126A mutation in rpST is achieved precisely as described for L118E, except that the mutagenic oligonucleotide employed in both the mutagenesis and hybridization/-screening reactions is A124-2, and the template DNA used for mutagenesis is pGEMpST-SX-I122L. The template DNA is prepared precisely as described for pGEMpST-SX DNA. Mutation-bearing plasmids are detected by incubating the nitrocellulose filters in TAC buffer at 56° C. The plasmid bearing this mutation, confirmed by DNA sequence analysis, is designated pGEMpST-SX-I122LM126A.

EXAMPLE 7

SUBSTITUTION OF AMINO ACID RESIDUES ON THE HYDROPHILIC SURFACE OF HELIX 3

The members of this mutational class include G121A, K114R, and K116R. The plasmids bearing these mutations are designated pGEMpST-SX-G121A, pGEMpST-SX-K114R and pGEMpST-SX-K116R, respectively. The construction of these mutations is performed precisely as described for L118E except for the mutagenic oligonucleotides employed and, if necessary, the TAC wash temperature.

The DNA sequence of the synthetic mutagenic oligonucleotide useful in the construction of mutation G121A, G121A/XmnI is displayed in Table I. This oligonucleotide alters the sequence of the rpST gene such that the codon for glycine at position 121 is converted from GGC to GCT which encodes alanine. This oligonucleotide also differs from the rpST DNA sequence so that an XmnI restriction recognition site (5'-GAAGCTATTC-3') is incorporated into the rpST DNA sequence. Except for the G121A mutation, the additional nucleotide changes do not result in changes in the amino acid sequence of the rpST protein. The G121A/XmnI oligonucleotide is also used as the radio-labelled detection probe in the hybridization reactions, which in all other respects are identical to those described above. Candidate mutation-bearing clones are detected by incubating the nitrocellulose filters in TAC buffer at 57.5° C. and by assaying for the acquisition of an XmnI site, which is present in the mutagenic oligonucleotide and is therefore diagnostic of the presence of the G121A mutation in the plasmid clone. The plasmid bearing this mutation, confirmed by DNA sequence analysis, is designated pGEMpST-SX-G121A.

The generation of the K114R mutation in rpST is achieved precisely as described for L118E, except that the mutagenic oligonucleotide employed in both the mutagenesis and hybridization/screening reactions is K114R/AccI whose sequence is displayed in Table I. The K114R/AccI oligonucleotide alters the rpST sequence so that the codon for lysine at position 114 is changed from AAG to CGT which encodes arginine. This oligonucleotide also differs from the rpST DNA sequence such that an AccI restriction recognition site (5'-GTATAC-3') is incorporated into the rpST DNA sequence. Except for the K114R mutation, the additional nucleotide changes do not result in changes in the amino acid sequence of the rpST protein. Like G121A, putative mutation-bearing clones are detected by incubating the nitrocellulose filters in TAC buffer at 57.5° C. and examined for acquisition of a new AccI restriction site which is present in the mutagenic oligonucleotide and is therefore diagnostic of the presence of the K114R mutation in the plasmid clone. The plasmid bearing this mutation, confirmed by DNA sequence analysis, is designated pGEMpST-SX-K114R.

The generation of the K116R mutation in rpST is achieved precisely as described for L118E, except that the mutagenic oligonucleotide employed in both the mutagenesis and hybridization/screening reactions is K116R/BglII whose sequence is displayed in Table 1. The K116R/BglII oligonucleotide alters the rpST sequence so that the codon for lysine at position 116 is changed from AAG to CGA which encodes arginine. This oligonucleotide also differs from the rpST DNA sequence so that a BglII restriction recognition site (5'-AGATCT-3') is incorporated into the rpST DNA sequence from positions 342–347 of the nucleotide sequence. Except for the K116R mutation, the additional nucleotide changes do not result in changes in the amino acid sequence of the rpST protein. Like G121A, putative mutation-bearing clones are detected by incubating the nitrocellulose filters in TAC at 57.5° C. and examined for the acquistion of a new BglII restriction site which is present in the mutagenic oligonucleotide and is therefore diagnostic of the presence of the K116R mutation in the plasmid clone. The plasmid bearing this mutation, confirmed by DNA sequence analysis, is designated pGEMpST-SX-K116R.

EXAMPLE 8

SUBSTITUTION OF HYDROPHILIC AMINO ACIDS IN HELIX 2 WITH HYDROPHOBIC AMINO ACID RESIDUES USING TWO SYNTHETIC OLIGONUCLEOTIDES SIMULTANEOUSLY

The member of this mutational class is the double mutation, S81,87L. The plasmid bearing this mutation, confirmed by DNA sequence analysis, is designated pGEMpST-SX-S81,87L. The DNA sequence of the synthetic mutagenic oligonucleotides, S81L and S87L, used in the construction of the double mutant S81,87L is given in Table I. The S81L and S87L oligonucleotides alter the sequence of the rpST gene such that the codon for serine at positions 81 and 87, respectively, are converted from TCG to TTG, which encodes leucine. The construction of this double mutant rpST gene is precisely as described for L118E except that both of the mutagenic oligonucleotides are used simultaneously in the mutagenesis reaction. The S81L oligonucleotide is also used as the radio-labelled detection probe in the hybridization reactions, which in all other respects are identical to those described for L118E, except that the filters are washed in TAC buffer at 54° C. Bacterial transformants carrying the putative positive mutation-bearing plasmid clones are selected, transferred to nitrocellulose filters and processed for hybridization. In this second round of screening, the S87L oligonucleotide is used as the radio-labelled probe; filters are washed in TAC buffer at 54° C.

EXAMPLE 9

SUBSTITUTION OF HYDROPHOBIC AMINO ACID RESIDUES IN HELIX 2 WITH HYDROPHILIC AMINO ACID RESIDUES

The single member of this mutational class is the double mutation, L82,84Q. The plasmid bearing this mutation, confirmed by DNA sequence analysis, is designated pGEMpST-SX-L82,84Q. The DNA sequence of the synthetic mutagenic oligonucleotide used in the construction of mutation L82,84Q is Q8082 and is displayed in Table I. This oligonucleotide alters the sequence of the rpST gene such that the codons for leucine at positions 82 and 84 are each converted from CTG and CTC, respectively, to CAG, which encodes glutamine. Mutation-bearing plasmids are detected by incubating the nitrocellulose filters in TAC buffer at 58° C.

EXAMPLE 10

CONSTRUCTION OF HELIX 2 AND HELIX 3 COMBINATION MUTATIONS

Several helix 3 mutations, I122L, M126A, and E119LQ123L, which either retain (I122L, M126A,) or increase (E119LQ123L) the hydrophobic character of the hydrophobic surface of helix 3 are combined with the hydrophobic helix 2 double mutation, S81,87L by the following subcloning reactions. Plasmid pGEMpST-SX-S81,87L is restricted with XbaI and EcoRI. The small fragment is purified by agarose gel electrophoresis and contains the S81,87L mutation. Plasmid pROpST-SXA-I122L is also restricted sequentially with XbaI and EcoRI, and the large fragment similarly is purfied. The large fragment carries the pROpST expression vector components and the pST mutations I122L and the cysteine to alanine substitutions at positions 183 and 191. This large fragment, and the small S81,87L fragment, are joined in the presence of T4 DNA ligase and ATP. Half of the reaction mixture is introduced into expression strain 4300, made competent by treatment with $CaCl_2$. Transformed cells are cultured overnight at 30° C. Plasmid-bearing cells are assayed for pST expression as described in Example 12; plasmid containing this helix 2/helix 3 combination is designated pROpST-SXA-S81,87L+I122L.

Combination mutations pROpST-SXA-S81,87L+M126A and pROpST-SXA-S81,87L+E119LQ123L are constructed precisely as described for pROpST-SXA-S81,87L+I122L, except that pROpST-SXA-M126A and pROpST-SXA-E119LQ123L are used as the source of the expression vector components and the helix 3 mutation(s) for generating pROpST-SXA-S81,87L+M126A and pROpST-SXA-E119LQ123L, respectively.

The helix 2 double mutation L82,84Q is combined with the helix 3 mutation L115K exactly as described for S81,87L+I122L except that the source of mutant helix 2 DNA is pGEMpST-SXA-82,84Q and the source of the helix 3 mutation. L115K, is pROpST-SXA-L115K. The plasmid containing this combination is designated pROpST-SXA-L82,84Q+L115K.

EXAMPLE 11

SUBSTITUTION OF HYDROPHOBIC AMINO ACIDS IN OR NEAR HELIX 1 WITH HYDROPHILIC AMINO ACIDS USING MUTAGENIC OLIGONUCLEOTIDES

The object of these mutations is to replace hydrophobic amino acid residues found in the $NH_2$-terminal portion of rpST with hydrophilic amino acid residues that are present in the same relative position of human growth hormone.

Members of this mutational class include the rpST double mutation Q21HH22R, double mutation S11RA14D and single mutations A6T and A14D. Plasmids bearing these mutations are confirmed by DNA sequence analysis and are designated pGEMpST-SX-Q21HH22R, pGEMpST-SX-S11RA14D, pGEMpST-SX-A6T and pGEMpST-SX-A14D, respectively. The construction of these mutations is performed precisely as described for L118E except for the mutagenic oligonucleotides employed, the incubation temberature of nitrocellulose filters in TAC buffer, and an additional screen for positive, mutation bearing plasmids by digestion with an appropriate restriction endonuclease, if and where appropriate.

The DNA sequence of the synthetic mutagenic oligonucleotide used in the construction of the double mutation Q21HH22R, Q21HH22R/ClaI, is displayed in Table I. This oligonucleotide alters the sequence of the rpST gene such that the codon for glutamine at position 21 is converted from CAG to CAT which encodes histidine, and the histidine at position 22 is converted from CAC to CGA, which encodes arginine. Embedded in these mutations is a ClaI restriction endonuclease cleavage site (5'-ATCGAT-3'), which is unique to the altered rpST gene. The Q21HH22R/ClaI oligonucleotide is also used as the radio-labelled detection probe in the hybridization reactions, which in all other respects are identical to those previously described. All of the procedures used in the construction of this mutation are as previously described for L118E, except that the filters are washed in TAC buffer at 56° C. Also, candidate mutation-bearing clones are assayed for the acquisition of a ClaI site, which is present in the mutagenic oligonucleotide and is therefore diagnostic of the presence of the Q21HH22R double mutation in the plasmid clone.

The generation of the A6T mutation in rpST is achieved precisely as described for L118E, except that the mutagenic oligonucleotide A6T, displayed in Table I is used in both the mutagenesis and hybridization reactions. The A6T oligonucleotide alters the rpST sequence so that the codon for alanine at position 6 is converted from GCC to ACC, which encodes threonine. Subsequent to hybridization, the bacterial-containing nitrocellulose filters are washed in TAC buffer at 52° C.

The generation of the S11RA14D double mutation is achieved precisely as described for L118E, except that mutagenic oligonucleotide S11RA14D/SalI is used in both the mutagenesis and hybridization reactions, and that the nitrocellulose filters are washed in and TAC buffer at 64° C. The S11RA14D/SalI oligonucleotide alters the rpST sequence such that the serine codon at position 11 is converted from AGC to CGA, which encodes arginine, and the alanine codon at position 14 is converted from GCC to GAC, which encodes aspartic acid. This oligonucleotide also differs from the rpST DNA sequence so that a SalI restriction recognition site (5'-GTCGAC-3') is incorporated into the rpST DNA sequence from positions 29–34 of the nucleotide sequence Except for the S11R and A14D mutations, the additional nucleotide changes do not result in changes in the amino acid sequence of the rpST protein. Putative mutation-bearing clones are examined for the acquisition of a new SalI restriction site which is present in the mutagenic oligonucleotide and is therefore diagnostic of the presence of the S11RA14D double mutation in the plasmid clone.

The generation of the A14D single mutation is achieved precisely as described for L118E, except that mutagenic oligonucleotide A14D/HindIII is used in both the mutagenesis and hybridization reactions. The A14D/HindIII oligonucleotide alters the rpST sequence such that the alanine codon at position 14 is converted from GCC to GAC, which encodes aspartic acid. This oligonucleotide also differs from the rpST DNA sequence so that a HindIII restriction recogintion site (5'-AAGCTT-3') is incorporated into the rpST DNA sequence from positions 30–35 of the nucleotide sequence. Except for the A14D mutation, the additional nucleotide changes do not result in changes in the amino acid sequence of the rpST protein. Putative mutation-bearing clones are detected by incubating the nitrocellulose filters in TAC buffer at 62° C. and examined for the acquisition of a new HindIII restriction site which is present in the mutagenic oligonucleotide and is therefore diagnostic of the presence of the A14D mutation in the plasmid clone.

EXAMPLE 12

RECONSTRUCTION OF pST MUTATIONS INTO APPROPRIATE BACTERIAL EXPRESSION PLASMIDS

The altered (mutation-bearing) clones are reconstructed into derivatives of the bacterial expression plasmid pRO211 (described in EPO173280 patent application incorporated herein by reference thereto), designated pROpST, pROpSTA34 and pROpSTE34. Plasmid pROpST contains pST DNA cloned into expression vector pRO211 and contains cysteine-encoding DNA at positions 183 and 191; pROpSTA34 contains alanine-encoding DNA and pROpSTE34 contains glutamic acid-encoding DNA at these positions. The pGEMpST altered clones are digested with EcoRI and SmaI and the small pST mutation-bearing fragment isolated. pROpSTA34 DNA is similarly treated, and the large, vector-containing DNA fragment is isolated. These purified fragments are ligated together with T4 DNA ligase and transformed into an appropriate bacterial strain, e.g. 4300. This strain contains a temperature sensitive λ repressor ($cI^{857}$, so that expression from the $\lambda P_L$ promoter is prevented at 30° C., but permitted at 42° C., at which temperature the repressor is inactivated. Introduction of altered pGEMpST DNA fragments into pROpSTE34 DNA is achieved precisely as described for pROpSTA34. Introduction of altered pGEMpST DNA fragments into pROpST is identical to that described for pROpSTA34, except that both pGEMpST and pROpSTA34 plasmids are digested with EcoRI and HindIII. Table II lists the bacterial expression plasmids into which the mutated pST genes are introduced. pST mutations A6T, S11RA14D and Q21HH22R are introduced into a derivative of pROpSTE34 as described for pROpSTE34. This derivative, $pROpSTE34T_1T_2$, contains a ca. 1 kb HindIII fragment at the 3' end of the pST coding DNA, which contains the transcription terminator $T_1T_2$ from the *E. coli* rrnB operon (the ribosomal RNA B operon).

TABLE II

EXPRESSION VECTOR CONSTRUCTIONS: AMINO ACID CONSTITUTION AT POSITIONS 183 AND 191

| | Amino acid encoded at 183 and 191 | | |
|---|---|---|---|
| Mutation | cysteine | alanine | glutamic acid |
| I122L | + | + | + |
| L115K | + | + | + |
| L118E | + | + | |
| L115KL118E | + | + | |
| L118EI122K | + | + | |
| L115E | | + | |
| I122E | + | + | |
| L118T | | + | |
| L118K | | + | |
| E119LQ123L | + | + | |
| L115A | + | + | |
| L118A | + | + | |
| M126A | + | + | |
| L118AI122L | | + | |
| I122LM126A | + | + | + |
| S81,87L | | + | |
| L82,84Q | | + | |
| S81,87L + E119LQ123L | | + | |
| " + I122L | | + | |
| " + M126A | | + | |
| L82,84Q + L115K | | + | |
| A14D | | | |
| A6T | | | +* |
| S11RA14D | | | +* |
| Q21HH22R | | | +* |
| A6TS11R | | | +* |

TABLE II-continued

| EXPRESSION VECTOR CONSTRUCTIONS: AMINO ACID CONSTITUTION AT POSITIONS 183 AND 191 | | | |
|---|---|---|---|
| | Amino acid encoded at 183 and 191 | | |
| Mutation | cysteine | alanine | glutamic acid |
| A6TS11R + I122L | | | + |
| P8TS11R + I122L | | | + |
| P8TS11R | | | + |

*Also contains the $T_1T_2$ transcription terminator sequence from the *E. coli* rrnB operon.

EXAMPLE 13

CONSTRUCTION OF HELIX 1 COMBINATION MUTANTS

A6TS11R+E34 AND P8TS11R+E34

Double mutation A6TS11R, in which the alanine at position 6 is replaced with threonine and serine at position 11 is replaced with arginine, is combined with the E34 mutations (described in EP355460), in which the DNA encoding cysteine at positions 183 and 191 are replaced with glutamic acid. The resultant rpST gene therefore contains mutations in both the $NH_2$-(A6TS11R) and COOH-encoding regions (E34) of the rpST DNA. The resulting plasmid is designated pROpSTE-A6TS11R. The altered, small, rpST-containing EcoRI/SmaI fragment from pML/pGH14, which contains the A6TS11R mutations, is joined to the large EcoRI/SmaI fragment from plasmid pROpSTE-$T_1T_2$. This latter plasmid is the pST expression plasmid, which also contains the strong transcription terminator from the *E. coli* rrnB operon ($T_1T_2$) at the 3' end of the rpST-encoding DNA.

Another double mutation, P8TS11R, in which the proline-encoding DNA at position 8 is mutated to encode threonine, and the serine-encoding DNA is mutated to encode arginine is combined with the E34 mutations (described in EP355460), in which the DNA encoding cysteine at positions 183 and 191 are replaced with glutamic acid. The resultant rpST gene therefore contains mutations in both the $NH_2$- (P8TS11R) and COOH-encoding regions (E34) of the rpST DNA. The resulting plasmid is designated pROpSTE-P8TS11R. The same strategy is employed in the construction of pROpSTE-P8TS11R as in pROpSTE-A6TS11R, except that plasmid pML/pGH18, which contains the P8TS11R double mutation is used as the source of the altered rpST DNA.

A6TS11R&I122L+E34 and P8TS11R+II12L+E34

The I112L helix 3 mutation described above is combined with each of the two helix 1 mutations, A6TS11R and P8TS11R and the E34 mutations. The resulting plasmids are designated pROpST-SXE-A6TS11R+I122L and pML/pGH18-SXE-I122L, respectively. pROpST-SXE-A6TS11R+I122L is constructed by joining the small I122L-containing BssHII/HindIII fragment with the large BssHII/HindIII fragment purified from pROpSTE-A6TS11R. This resulting plasmid contains the helix 2 cassette, defined by the SacI and XbaI restriction sites that flank the 5' and 3' ends of helix 2-encoding DNA previously described but does not contain the $T_1T_2$ transcription terminator. Plasmid pML/pGH18-SXE-I122L is constructed in an identical fashion except that plasmid pML/pGH18 is used as the source of the large fragment, carrying the P8TS11R double mutations. This altered plasmid does not contain the $T_1T_2$ transcription terminator, and does carry the helix 2 cassette.

EXAMPLE 14

STABILITY PROFILES OF MODIFIED RECOMBINANT SOMATOTROPINS

The procedure described to determine stability profiles is as follows. The concentrated solution of the recombinant (animal) somatotropin derivative (up to 100 mg/ml) in phosphate buffered saline pH 7.4 ($NaH_2PO_4H_2O$ 3.45gm, Na 3.55 gm, NaCl 9.50 gm dissolved in distrilled water 1,000 ml) is prepared. This is filtered through a millipore sterile Millex-0.22 μm filter unit and 0.1 ml aliquots placed into tubes. These are placed in a 43° C. oven and removed at the required intervals. The contents are then diluted with phosphate buffered saline. The supernatant is assayed for monomer and dimer content by HPLC. A mass balance is done. Any precipitated material is recorded. Results are compared with the initial concentrations and a stability profile documented.

Alternately, a somatotropin derivative exhibiting poor solubility at pH 7.4 is dissolved at a less preferred pH (4–10) or is evaluated as a suspension.

The results of solution stability studies for the altered rpST proteins are summarized in Table III.

TABLE III

| rpST MUTANT PROTEIN SOLUBILITY IN VITRO | | |
|---|---|---|
| Mutation | % Soluble | Days Incubated at 43° C. |
| A34 | 32 | 14 |
| I122L + A34 | 44 | 14 |
| E34 | 70.0(3) | 14 |
| | 67 | 17 |
| I122L + E34 | 62.0(2) | 14 |
| | 66.3(3) | 17 |
| A6TS11R + E34 | 68.5(2) | 14 |
| P8TS11R + E34 | 62 | 14 |
| A6TS11R + I122L + E34 | 36 | 14 |
| P8TS11R + I122L + E34 | 2 | 14 |
| L118K + A34 | 0 | 3 |
| E119LQ123L + A34 | 0 | 3 |
| L115A + A34 | 0 | 3 |
| L118A + A34 | 10 | 7 |
| M126A + A34 | 18 | 3 |
| L118AI122L + A34 | 2 | 7 |
| I122LM126A + A34 | 22(2) | 19 |
| S81,87L + A34 | 0 | 3 |
| S81,87L + E119LQ123L + A34 | 0 | 7 |
| S81,87L + I122L + A34 | 8 | 7 |
| S81,87L + M126A + A34 | 0 | 3 |

Percent solubility is expressed as the fraction of the total remaining in solution × 100. (See Example 14). Where more than one determination is made, an average % solubility is presented, and the number of independent determinations is given in parentheses. The rpST mutants are present in either the A34 or E34 backgrounds. A34 rpST contains alanine, instead of cysteine, at positions 183 and 191. E34 rpST contains glutamate instead of cysteine at positions 183 and 191.

EXAMPLE 15

HYPOX RAT TEST METHOD FOR DETERMINING THE GROWTH ENHANCEMENT OF ANIMALS RECEIVING RECOMBINANT (ANIMAL) SOMATOTROPIN DERIVATIVE

The efficacy of the recombinant animal somatotropin derivatives of the present invention for altering the growth rate of animals is determined utilizing the hypophysectomized (hypox) rat assay. The hypophysectomized rat does not produce its own somatotropin and is sensitive to injected somatotropin. The response measured is growth over a period of time such as 10 days and is presented in Table IV as percent of the biological activity of the rpST positive control, which is included in every trial.

TABLE IV

BIOLOGICAL DATA (HYPOX RAT, RRA) AND THERMAL STABILITY FOR rpST MUTANT PROTEINS

| Mutation(s) | Hypox rat[a] | RRA[b] | $T_{(m)}$(°C.) |
|---|---|---|---|
| A34 | 112.8 | 173.5 | nd |
| I122L + A34 | 97.4 | 225.8 | 79 |
| E34 | 90.52(5) | 51.4(7) | 62.0(6) |
| I122L + E34 | 66.66(5) | 80.28(5) | 62.67(5) |
| L115K | 0.3 | 1.2 | >83 |
| L115K + E34 | 0.8 | 0.9 | 79 |
| L118K | 1.8 | 43.9 | 36 |
| E119LQ123L | 33.8 | 80.2 | 49 |
| L115A | 88.6 | 163 | 50 |
| L118A | 64(3) | 49.5 | 57 |
| M126A | 100 | 122 | 55 |
| L118AI122L | 38.9 | 57.9 | 56 |
| I122LM126A | 66.25(2) | 82.55(2) | 63 |
| S81,87L | 46.9 | 194 | 40 |
| S81,87L + E119LQ123L | 40.4 | 177.9 | 38 |
| S81,87L + I122L | 71.3 | 165 | 47 |
| S81,87L + M126A | 79.7 | 186 | 47 |
| L82,84Q | 9.7(2) | 3.4 | none observe |
| K114R + E34 | 121.3 | 53.2 | 62 |
| A6TSllR + E34 | 80.7(4) | 135.0(4) | 64.0(4) |
| P8TS11R + E34 | 129.7 | 78.5 | 65 |
| A6TS11R + I122L + E34 | 116.7 | 112.8 | 61 |
| P8TS11R + I1221 + E34 | 127.9 | 89.3 | 64 |

[a]Hypox rat results are given as percent of the activity of the rpST standard used as the positive control.
[b]RRA-Liver radio-receptor assay results are given as percent of the activity observed with the rpST standard.
nd: not determined
Where more than one determination is made, an average is given, with the number of determinations given in parentheses.

EXAMPLE 16

LIVER RADIO-RECEPTOR ASSAY FOR DETERMINING ABILITY OF ALTERED RECOMBINANT SOMATOTROPIN TO BIND TO SOMATOTROPIN RECEPTOR IN VITRO

An in vitro radioreceptor assay is employed to assess the ability of the recombinant somatotropins of the present invention to compete with $^{125}$I-rpST for binding to somatotropin receptor from purified liver membranes. The results of these assays are given as percent rpST binding and are presented in Table IV.

EXAMPLE 17

NITROGEN BALANCE EXPERIMENTS CONDUCTED WITH rpST MUTANT I122L+E34

To evaluate biological activity of altered rpST proteins carrying the I122L mutation in vivo, a nitrogen balance study is conducted as described in EP355460. Subcutaneous administration of pST to growing pigs increases the quantity of protein deposited in the body, primarily as muscle. The use of a nitrogen balance test provides a measure of the change in amount of protein deposited by an animal. Since protein contains a fixed amount of nitrogen, analyzing feedstuffs and excreta for nitrogen provide an accurate estimate of the status of protein deposition. Thus, nitrogen balance is a measure of the amount of nitrogen consumed in the feed and the amount excreted in the urine and feces with the amount retained (deposited) calculated by difference. Nitrogen retention is most accurately estimated as the amount of nitrogen retained as a percentage of the amount of nitrogen digested (nitrogen consumed minus fecal nitrogen). In this study, the cysteine residues at positions 183 and 191 or the rpST I122L variant have been replaced with glutamic acid. The results of this analysis demonstrate full biological activity of the altered rpST molecule relative to the rpST control.

EXAMPLE 18

DETERMINATION OF THERMAL STABILITY USING FLUORESCENCE SPECTROSCOPY

The thermal stability of altered rpST is inferred from measuring the intrinsic tryptophan fluorescence as a function of temperature. The rpST molecule contains a single tryptophan residue, whose intrinsic fluorescence is severely quenched in the "native state". Increasing temperature, or decreasing pH, causes a characteristic increase in fluorescence, which is presumably due to a loss of structure at least in the immediate vicinity of the otherwise buried tryptophan residue. A "melting profile" of fluorescence versus increasing temperature reveals a sigmoidal curve, in which fluorescence remains quenched up until a temperature that is characteristic for a given rpST derivative. A sharp increase in fluorescence over a rather narrow temperature range then ensues. The temperature that defines the midpoint of this increase in fluorescence is designated $T_{(m)}$ and is a reflection of the protein's thermal stability. The $T_{(m)}$ of the rpST of the present invention is determined by the method of Burger, et al 1966, except that 295 nm is used as the excitation wavelength and the emission fluorescence is read using a 355 nm cut off filter. The $T_{(m)}$ of the rpST of the present invention is summarized in Table IV. These data reveal a marked increase in $T_{(m)}$ of 79° C. for I122L.

EXAMPLE 19

GENERATION OF THE I122L MUTATION BY THE POLYMERASE CHAIN REACTION METHOD

The I122L mutation is introduced into the rpST gene by site-directed mutagenesis utilizing an application of polymerase chain reaction technology as described by Sarkar and Sommer 1990, incorporated herein by reference. The three oligonucleotide primers used are listed in Table I and include oligonucleotides SacI293, L120-3 and PvuII634. The rpST gene-containing EcoRI/HindIII fragment from plasmid pGEMpST-SX is used as the template. Fifteen cycles of polymerase chain reaction (hereafter referred to as PCR) is performed on 1 ng template rpST DNA with 1 μM each of the L120-3 and PvuII634 oligonucleotide primers, dNTP's and Taq DNA polymerase, as specified by the manufacturer. This reaction results in a 227 bp DNA fragment, which contains the I122L mutation. This fragment is purified by agarose gel electrophoresis and is used as a PCR primer in combination with oligonucleotide primer SacI293 and the rpST-containing EcoRI/HindIII template fragment in 15 additional cycles of PCR. The resultant 361 bp fragment is cleaved with restriction endonucleases SacI and PvuII, purified by agarose gel electrophoresis and ligated into the large gel-purified, SacI/PvuII pGEMpST-SX DNA fragment. The ligation mixture is transformed into HB101 competent cells. Plasmid DNA of the resulting transformants is screened for the presence of the I122L mutation precisely as described for L118E, except that oligonucleotide L120-3 is used as the radio-labelled hybridization probe and only one round of screening is performed. The presence of the I122L mutation and the absence of additional mutations introduced by the PCR reactions is confirmed by DNA sequence analysis. The plasmid bearing this mutation is designated pGEMpST-SX-I122L$_{PCR}$.

EXAMPLE 20

RECONSTRUCTION OF rpST MUTATION I122L INTO A PLASMID SUITABLE FOR EXPRESSION IN YEAST

Figure 5:
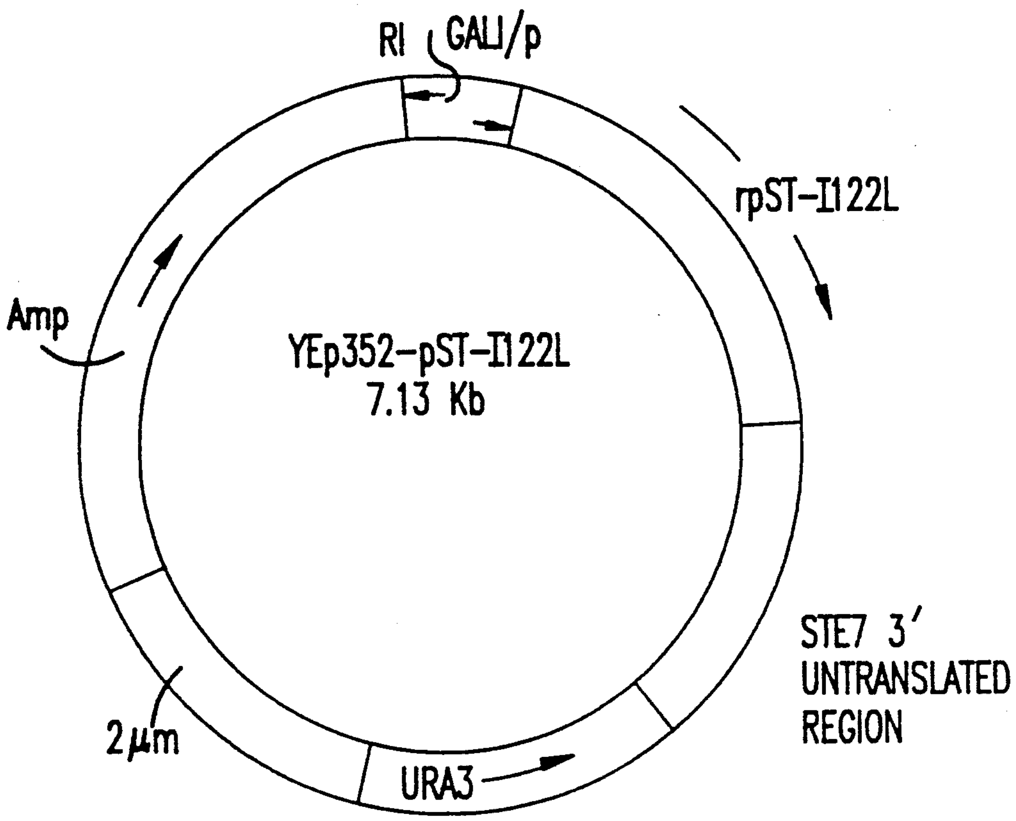
FIG. 5: Structure of yeast expression plasmid YEp352-pST-I122L. This plasmid is a derivative of YEp352 and contains the rpST mutation, I122L, whose expression is driven by the inducible GAL1/GAL10 promoter from *S. cerevisiae.* The 3' untranslated DNA is derived from the yeast STE7 gene. The 2 μm element supports plasmid replication in yeast, and the URA3 provides a selectable marker for the transformant selection in yeast. This plasmid also carries the pBR322 origin of replication (not shown) and the ampicillin resistance gene.

In order to express the I122L mutation-bearing rpST gene in the yeast, *Saccharomyces cerevisiae,* the rpST encoding DNA must be operably linked to a promoter sequence derived from this yeast. The ends of the small rpST-bearing NdeI/HindIII fragment from pROpST-SXE-I122L are made flush by treatment of this DNA with the large Klenow fragment of DNA polymerase I after the plasmid is cleaved with NdeI and HindIII. This fragment is purified by gel electrophoresis and joined with the large SalI/SphI fragment of plasmid is YEp352-2. The ends of this latter fragment are made flush by treatment with S1 nuclease. This plasmid is a YEp352-derivative, which has been modified to additionally contain the divergent GAL1/GAL10 promoter (Johnston and Davis, 1984), and the 3' untranslated region derived from the STE7 gene (Teague, et al, 1986). The resulting plasmid is designated YEp352-pST-I122L (FIG. 5).

Expression of this rpST variant in yeast is accomplished by culturing yeast cells transformed with this plasmid in a synthetic complete medium (Sherman, Fink and Hilks, 1986) that lacks uracil and contains 2% galactose as the sole carbon source at 30° C. for several hours, or however necessary to achieve maximal rpST gene induction and rpST production. Although any yeast strain carrying a mutation in the URA3 gene can be used as the host, it is preferable to employ a yeast strain that is deficient in protease production and is GAL+, such as BJ5457 (genotype MATα pep4::HIS3 prb1-Δ trp1 ura3-52 leu2-Δ his3-Δ lys2-801 can1 GAL+). This strain is deposited with the Yeast Genetic Stock Center, University of California, as BJ5457.

BIBLOGRAPHY

1. Abdel-Meguid et al. (1987)., *Proc. Natl. Acad. Sci.* U.S.A. 84, 6434–6437
2. Brems, *Biochemistry* 27, 4541–4546 (1988).
3. Brems et al. (1986), *Biochemistry* 25, 6539–6543.
4. Brems et al (1988), *Proc. Natl. Acad. Sci.* U.S.A. 84, 3367–3371 .
5. Burger, H. G., Edelhoch, H. and Condliffe, P. G., (1966) *Endocrinology* 78, 98–102.
6. Chen, W. Y. et al. (1990), *Proc. Natl. Acad. Sci* U.S.A. 87, 5061–5065.
7. Johnston and Davis, (1984) *Molecular and Cellular Biology* 4, 1440–1448.
8. Sarkar and Sommer, *Biotechniques* 8, 404–407 (1990).
9. Teague et al (1986), *Proc. Nat. Acad. Sci* U.S.A. 83, 7371–7375.
10. Sherman, F., Fink, G. R. and Hicks, J. B., (1986) "Laboratory Course Manual for methods in yeast genetics," Cold Spring Harbor Laboratory, Cold Spring Harbor, N.Y. pp 163–168.

What is claimed is:

1. A somatotropin in which the alpha-helix 3 region is mutated, thereby enhancing the aqueous solubility of said somatotropin over the aqueous solubility of the native alpha-helix 3 form of said somatotropin while maintaining biological activity in a sustained release formulation.

2. The somatotropin according to claim 1, wherein said somatotropin is human, bovine, porcine, ovine, caprine, equine, fish or avian somatotropin.

3. The somatotropin according to claim 2, wherein said alpha-helix 3 mutation is I122L, in which the isoleucine at position 122 in alpha-helix 3 is replaced with leucine.

4. The somatotropin according to claim 3, wherein said somatotropin is porcine or bovine somatotropin.

5. The somatotropin according to claim 4, wherein said somatotropin is porcine somatotropin.

6. The somatotropin according to claim 1, wherein of the four (4)cysteines, two in the small loop and two in the large loop, at least one (1) is deleted.

7. The somatotropin according to claim 1, wherein four cysteines are modified to cysteic acid.

8. The somatotropin according to claim 3, wherein the cysteines at positions 183 and 191 are replaced by glutamic acid.

9. The somatotropin according to claim 3, wherein of the four (4) cysteines, two in the small loop and two in the large loop, at least one (1) is deleted.

10. The somatotropin according to claim 3, wherein four cysteines are modified to cysteic acid.

* * * * *